United States Patent [19]

Cabardo, Jr.

[11] 4,414,203

[45] Nov. 8, 1983

[54] PERIODONTAL POWDER CONTAINING EXSICCATED POTASSIUM ALUM

[76] Inventor: Alberto M. Cabardo, Jr., 197 N. Washington St., Battle Creek, Mich. 49016

[21] Appl. No.: 255,031

[22] Filed: Apr. 16, 1981

Related U.S. Application Data

[60] Division of Ser. No. 848,802, Nov. 7, 1977, Pat. No. 4,276,287, which is a continuation of Ser. No. 618,618, Apr. 29, 1976, abandoned, which is a continuation-in-part of Ser. No. 256,388, May 24, 1972, abandoned.

[51] Int. Cl.$^3$ .................... A61K 33/06; A61K 7/16; A61K 33/00; A61K 7/24
[52] U.S. Cl. .................... 424/154; 424/49; 424/55; 424/58; 424/127; 424/195; 424/270
[58] Field of Search .................... 424/154, 49, 55, 58, 424/127, 195, 270

[56] References Cited

PUBLICATIONS

Principles & Practice of Modern Cosmetics 2, (23) (1963) Chem. Publ. Co., Inc., N.Y.
Accepted Dental Remedies 32nd ed., pp. 156, 175 and 177 (1967)–American Dental Assoc.
Accepted Dental Therapeutics 33rd ed. pp. 185–186 (1969–1970) American Dental Assoc.
Accepted Dental Therapeutics 34th ed. pp. 199–200 and 253 (1971–1972)–American Dental Assoc.

*Primary Examiner*—Douglas W. Robinson
*Attorney, Agent, or Firm*—Lockwood, Dewey, Alex & Cummings

[57] ABSTRACT

A powder for the treatment of periodontal disorders comprises a mixture of evenly exsiccated potassium alum and sodium bicarbonate in a ratio, by weight, of approximately 2:1 of the potassium alum to sodium bicarbonate. The powder may be mixed with sufficient liquid to form a paste and flavoring, sweetening, coloring, scenting and antiseptic ingredients may be added.

18 Claims, 4 Drawing Figures

```
POWDER:  EVENLY EXSICCATED POTASSIUM ALUM.——288GM.
         SODIUM BICARBONATE————————————144 GM.
         SODIUM SACCHARIN, N., F.——————————1.2.GM.
LIQUID:  METHYL SALICYLATE, U.S.P.—————————5CC.
         EUCALYPTUS OIL, U.S.P.—————————————6CC.
         ANISE OIL, U.S.P.——————————————————5CC.
         OIL OF PEPPERMINT, U.S.P.—————————6CC.
         CERTIFIED FOOD COLOR—————————————5gtts.
```

```
MIX POTASSIUM ALUM. AND SODIUM BICARBONATE.
ADD METHYL SALICYLATE, ADD EUCALYPTUS OIL.
MIX SACCHARIN WITH 5 DROPS OF CERTIFIED FOOD
COLOR AND ADD TO THIS, ONE TBSP. OF ABOVE MIXTURE. BLEND WITH
REMAINING MIXTURE ADD ANISE OIL, AND THEN ADD OIL OF
PEPPERMINT
```

FIG.1.

50 G.M BY WEIGHT BEFORE EXSICCATION AT 350 DEGREES F ONE HOUR EXPOSURE.

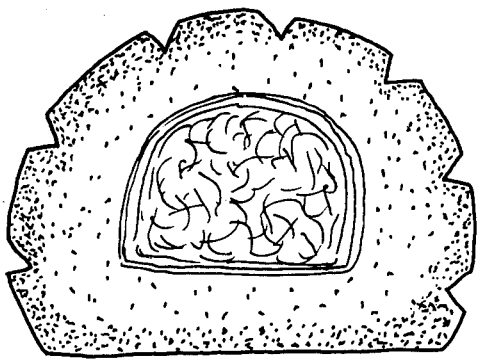

UNEVENLY EXSICCATED

FIG.2.

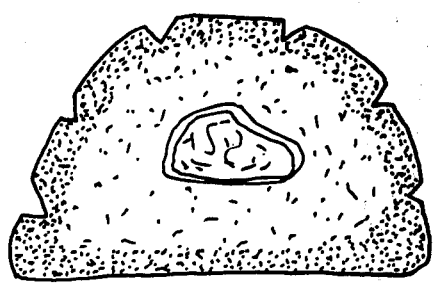

UNEVENLY EXSICCATED

FIG.3.

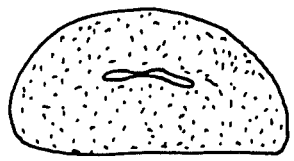

10 GM BY WEIGHT BEFORE EXSICCATION AT 350F EXPOSURE 1 HOUR EVENLY EXSICCATED

FIG.4.

PERIODONTAL POWDER CONTAINING EXSICCATED POTASSIUM ALUM

RELATED APPLICATIONS

This application is a division of application Ser. No. 848,802, filed Nov. 7, 1977, now U.S. Pat. No. 4,276,287, which application was a continuation application of application Ser. No. 618,618, filed Apr. 29, 1976, now abandoned. which latter application was a continuation-in-part application of application Ser. No. 256,388, filed May 24, 1972, now abandoned.

BACKGROUND OF THE INVENTION

The present invention relates to a periodontal powder and a method of making same.

An object of the invention is to provide a method of making a periodontal powder which is simple in execution.

Another object of the invention is to provide a periodontal powder which is a potent aid to periodontal therapy, controls simple gum bleeding and is a considerable aid in the treatment of chronic and acute gingivitis.

These and other objects, features and advantages of the present invention will be more clearly understood through a consideration of the following detailed description.

BRIEF DESCRIPTION OF THE DRAWING

In order that the invention may be readily carried into effect, it will now be described with reference to the accompanying drawing, wherein:

FIG. 1 is a flow chart of the method of making the composition of the invention;

FIGS. 2 and 3 are cross-sectional views of unevenly exsiccated potassium alum powder; and FIG. 4 is a cross-sectional view of evenly exsiccated potassium alum powder.

DESCRIPTION OF THE PREFERRED EMBODIMENTS

The periodontal powder and method of my invention comprises mixing evenly exsiccated potassium alum powder and sodium bicarbonate powder in a ratio, by weight, of approximately 2:1 potassium alum to sodium bicarbonate.

By way of example, 228 grams of evenly exsiccated potassium alum powder may be mixed as shown in the drawing with 144 grams of sodium bicarbonate powder. 5 cc of liquid methyl salicylate may be added. 6 cc of eucalyptus oil may also be added.

Five drops of certified food color is mixed with 1.2 grams of sodium saccharin powder. The sodium saccharin and food color may be added to one tablespoonful of the potassium alum, sodium bicarbonate, methyl salicylate, eucalyptus oil mixture to provide a sub-mixture. The sub-mixture is blended with the remaining mixture of potassium alum, sodium bicarbonate, methyl salicylate and eucalyptus oil.

5 cc of anise oil may also be added to the resultant mixture. 6 cc of oil of peppermint may also be added to the mixture.

The principal chemical agent is the evenly exsiccated potassium alum powder. The base chemical is sodium bicarbonate. Eucalyptus oil and methyl salicylate may be included for their antiseptic properties. Oil of peppermint and anise oil may be utilized to provide flavoring. Saccharin may be added for sweetening. Food coloring may be provided for attractive coloring.

The mixing throughout the process is thorough and well executed. The mixture at each stage is even and smooth.

The resultant mixture is permitted to stand one half to one hour, or a little longer, before the periodontal powder is packed and permanently sealed. This eliminates or minimizes pressure within the container.

The periodontal powder is useful as tooth powder in brushing the teeth and massaging the gums. For simple bleeding of gums and/or swollen gums, the periodontal powder is mixed with enough water to make a paste. A cotton swab is utilized to apply the paste to tender, swollen or bleeding areas by pressing gently, but firmly against the gum tissue. This should be done two or three times daily.

While the invention has been described by means of specific examples and in specific embodiments; I do not wish to be limited thereto, for obvious modifications will occur to those skilled in the art without departing from the spirit and scope of the invention.

What I claim is:

1. A periodontal powder composition useful in periodontal treatment comprising a mixture of evenly exsiccated potassium alum and sodium bicarbonate in a ratio, by weight, of approximately 2:1 of said potassium alum to said sodium bicarbonate.

2. The composition of claim 1 further including at least one antiseptic agent.

3. The composition of claim 2, wherein said antiseptic agent is selected from the group consisting of methyl salicylate, eucalyptus oil and mixtures thereof.

4. The composition of claim 1 further including at least one flavoring agent.

5. The composition of claim 4, wherein said flavoring agent includes a material selected from the group consisting of oil of peppermint, anise oil and mixtures thereof.

6. The composition of claim 1 further including at least one sweetening agent.

7. The composition of claim 6 wherein said sweetening agent is saccharin.

8. The composition of claim 1 further including a coloring agent.

9. The composition of claim 8 wherein said coloring agent is a food coloring.

10. The composition of claim 1 further including at least one antiseptic agent, at least one flavoring agent, at least one sweetening agent and at least one coloring agent.

11. The composition of claim 10 wherein said antiseptic agent is selected from the group consisting of methyl salicylate, eucalyptus oil and mixtures thereof, said flavoring agent is selected from the group consisting of oil of peppermint, anise oil and mixtures thereof, said sweetening agent is saccharin, and said coloring agent is a food color.

12. The composition of claim 1 comprising a mixture of materials in proportion to the following:
   approximately 288 grams of said finely exsiccated potassium alum;
   approximately 144 grams of said sodium bicarbonate;
   aproximately 5 cc of methyl salicylate;
   approximately 6 cc of eucalyptus oil;
   approximately 1.2 grams of sodium saccharin;
   approximately 5 drops of certified food color;
   approximately 5 cc of anise oil; and approximately 6 cc of oil of peppermint.

13. The composition of claim 1 including an amount of liquid sufficient to form a paste of said powder.

14. The composition of claim 3 including an amount of liquid sufficient to form a paste of said powder.

15. The composition of claim 5 including an amount of liquid sufficient to form a paste of said powder.

16. The composition of claim 10 incuding an amount of liquid sufficient to form a paste of said powder.

17. The composition of claim 11 including an amount of liquid sufficient to form a paste of said powder.

18. The composition of claim 12 including an amount of liquid sufficient to form a paste of said powder.

* * * * *

UNITED STATES PATENT AND TRADEMARK OFFICE
CERTIFICATE OF CORRECTION

PATENT NO. : 4,414,203
DATED : November 8, 1983
INVENTOR(S) : Alberto M. Cabardo, Jr.

It is certified that error appears in the above-identified patent and that said Letters Patent are hereby corrected as shown below:

Column 1, line 10, after "abandoned", delete "."
and insert --,--.

Column 4, line 1 - delete "incuding" and insert
--including--.

Signed and Sealed this

Tenth Day of January 1984

[SEAL]

Attest:

GERALD J. MOSSINGHOFF

Attesting Officer     Commissioner of Patents and Trademarks